(12) United States Patent
Chen

(10) Patent No.: US 6,675,044 B2
(45) Date of Patent: Jan. 6, 2004

(54) SOFTWARE-BASED RECORD MANAGEMENT SYSTEM WITH ACCESS TO TIME-LINE ORDERED CLINICAL DATA ACQUIRED BY AN IMPLANTED DEVICE

(75) Inventor: Yuemean Chen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 212 days.

(21) Appl. No.: 09/850,330

(22) Filed: May 7, 2001

(65) Prior Publication Data

US 2002/0165437 A1 Nov. 7, 2002

(51) Int. Cl.⁷ .............................. A61N 1/37; A61B 5/044
(52) U.S. Cl. ......................... 607/30; 600/523; 600/525
(58) Field of Search .............................. 607/4, 30, 32, 607/60; 128/903; 600/523, 525

(56) References Cited

U.S. PATENT DOCUMENTS

| | | | |
|---|---|---|---|
| 4,316,472 A | | 2/1982 | Mirowski et al. ........ 128/419 D |
| 4,375,817 A | | 3/1983 | Engle et al. ............ 128/419 D |
| 4,384,585 A | | 5/1983 | Zipes .................... 128/419 D |
| 4,577,633 A | | 3/1986 | Berkovits et al. ..... 128/419 PG |
| 4,587,970 A | | 5/1986 | Holley et al. ......... 128/419 PG |
| 4,726,380 A | | 2/1988 | Vollmann et al. ..... 128/419 PG |
| 4,727,380 A | | 2/1988 | Miura et al. ................ 346/108 |
| 4,727,877 A | | 3/1988 | Kallok .................... 128/419 D |
| 4,800,883 A | | 1/1989 | Winstrom ................ 128/419 D |
| 4,830,006 A | | 5/1989 | Haluska et al. ....... 128/419 PG |
| 4,880,005 A | | 11/1989 | Pless et al. ........... 128/419 PG |
| 4,932,407 A | * | 6/1990 | Williams ................ 128/419 D |
| 4,949,719 A | * | 8/1990 | Pless et al. ............. 128/419 D |
| 4,953,551 A | * | 9/1990 | Mehra et al. ........... 128/419 D |
| 5,117,824 A | * | 6/1992 | Keimel et al. .......... 128/419 D |
| 5,163,427 A | * | 11/1992 | Keimel et al. .......... 128/419 D |
| 5,174,288 A | * | 12/1992 | Bardy et al. ............ 128/419 D |
| 5,188,105 A | * | 2/1993 | Keimel .................... 128/419 D |
| 5,261,400 A | * | 11/1993 | Bardy ........................... 607/5 |
| 5,345,362 A | * | 9/1994 | Winkler ....................... 361/681 |
| 5,350,411 A | * | 9/1994 | Ryan et al. ..................... 607/32 |
| 5,372,607 A | * | 12/1994 | Stone et al. .................... 607/30 |
| 5,697,959 A | * | 12/1997 | Poore ............................ 607/32 |
| 5,713,937 A | * | 2/1998 | Nappholz et al. ............. 607/30 |
| 5,716,384 A | * | 2/1998 | Snell ............................. 607/30 |
| 5,743,268 A | * | 4/1998 | Kabal ......................... 128/691 |
| 5,749,908 A | * | 5/1998 | Snell ............................. 607/30 |
| 5,819,741 A | * | 10/1998 | Karlsson et al. ............. 128/710 |
| 5,833,623 A | * | 11/1998 | Mann et al. .................. 600/523 |
| 5,921,938 A | * | 7/1999 | Aoyama et al. ............. 600/509 |
| 5,974,341 A | * | 10/1999 | Er et al. ........................ 607/31 |
| 6,016,442 A | * | 1/2000 | Hsu et al. ..................... 600/518 |
| 6,038,476 A | * | 3/2000 | Schwartz ...................... 607/27 |
| 6,091,990 A | * | 7/2000 | Hsu et al. ........................ 607/5 |
| 6,102,874 A | * | 8/2000 | Stone et al. ................. 600/595 |
| 6,161,039 A | * | 12/2000 | Krichen et al. ............. 600/523 |
| 6,308,100 B1 | * | 10/2001 | Er et al. ........................ 607/31 |
| 6,325,756 B1 | * | 12/2001 | Webb et al. ................ 600/300 |
| 6,415,175 B1 | * | 7/2002 | Conley et al. .............. 600/523 |

FOREIGN PATENT DOCUMENTS

| | | | |
|---|---|---|---|
| WO | 9218198 | 10/1992 | ............ A61N/1/39 |
| WO | 9829160 | 7/1998 | .......... A61N/1/372 |

OTHER PUBLICATIONS

Medtronic Kappa 700/600 Series Pacemaker Programming Guide.
Medtronic GEM II DR 7273 Dual Chamber Implantable Cardioverter Defibrillator System Reference Guide.

* cited by examiner

*Primary Examiner*—Carlo Layno
(74) *Attorney, Agent, or Firm*—Girma Wolde-Michael; Daniel G. Chapnik (57) ABSTRACT

A software-based medical data record management system includes access to time-line ordered clinical data acquired/ stored by at least one implanted device. The system enables data management categorized in relation to the time cardiac episodes and events were captured by the at least one implanted device. An interactive screen display is implemented to enable users to review therapy, diagnosis and medical device data on a time-line basis.

16 Claims, 7 Drawing Sheets

SOFTWARE-BASED RECORD MANAGEMENT SYSTEM WITH ACCESS TO TIME-LINE ORDERED CLINICAL DATA ACQUIRED BY AN IMPLANTED DEVICE

FIELD OF THE INVENTION

The present invention relates generally to implantable medical devices, such as implantable cardiac pacemakers, implantable cardioverter/defibrillators (ICD's), heart monitors, or any other medical device that stores therapy and diagnostic data for subsequent retrieval and display by an external instrument, device or programmer. More particularly, the invention relates to a software-based system, including a user interface, which orders diagnostic data in a time-line approach related to significant milestones such as events occurring, for example, at implant, during post-implant therapy and diagnostic follow-up sessions. The use of this system enables a physician to rapidly and accurately retrieve, evaluate and process relevant diagnostic and therapeutic data acquired and stored by the implantable device.

BACKGROUND OF THE INVENTION

Many types of implantable medical devices have been developed since 1960, including single and dual chamber pacemakers, pacemaker-cardioverter-defibrillators (PCDs), and implantable cardioverter-defibrillators (ICDs). All of these devices deliver therapies based on automatic diagnostic evaluations of cardiac activity. Further, these devices store event, diagnostic and therapy data in addition to the control of other operations. Moreover, these devices are programmable to change both their functional and operational parameters to match patient diagnostic and therapy needs.

Accordingly, cardiac devices have become progressively more sophisticated and capable of performing complex operations in response to a variety of inputs. The processing and operating control systems of such cardiac stimulators and monitors typically include a memory for storing operating modes and parameter values as well as keeping track of delivered therapies and diagnostic events related to the treatment of cardiac disease.

Implantable devices generally store a wide variety of different types of diagnostic data that assist a physician in evaluating both a patient's cardiac function and the operation of the implanted device. The specific collections or "records" of diagnostic data stored by the implanted device may be generally divided into three distinct categories: a) device-related, such as rate histograms to record paced and/or sensed rates over a complete rate range; b) patient-related such as atrial and/or ventricular tachyarrhythmia monitors; and c) therapy-related, such as mode switch, cardioversion, or defibrillation therapies. The number of these different records of diagnostic data in any one category can be quite high—often in the range of hundreds or more. Such information is useful not only in optimizing device programming but also in the management of the patient's arrhythmias and other cardiac/physiological conditions.

Often, the implantable device stores intracardiac electrogram ("IEGM") data preceding or following a detected arrhythmia along with the device's response to that arrhythmia, such as a defibrillation or cardioversion pulse. Cardiac stimulators typically process patient electrograms (EGMs) and acquire or measure physiological data for diagnosis. Such data is usually stored, especially if they relate to intrinsic heart rate or arrhythmic episodes. Stored data may be subsequently uplinked by telemetric means and displayed by interrogating the device memory using an external programmer. Such telemetered data are then analyzed, and may be employed to establish or refine the operating modes and parameters of the device operating algorithms. For example, the implantable device may be re-programmed to operate in a new mode or a new parameter value may be downloaded into memory to improve therapy response time.

A wide variety of programming and interrogation techniques have been devised for implantable medical devices. An example of a current medical device programmer is the Model 9790 universal programmer for bradycardia pacemakers and tachyarrhythmia devices. This device is described in U.S. Pat. Nos. 5,372,607, 5,345,362, and 5,350,411. The foregoing patents are hereby incorporated herein by reference in their respective entireties.

The "Medtronic Kappa® Pacemaker Programming Guide" published by Medtronic®, Inc. for the Kappa 700/600 Series Pacemakers, describes the operation of a typical modem pacemaker, and is incorporated herein in its entirety. The "Gem® II DR System Reference Guide" also published by Medtronic, Inc. for the operation and programming of the 7273 Gem II DR dual chamber implantable cardioverter defibrillator describes the operation of a typical modern ICD.

The various records of diagnostic data may be retrieved from the implantable device for display and evaluation, for example, using a programmer, which uses telemetry to communicate with the implanted device and download diagnostic data. This operation typically occurs during routine follow-up visits of the patient to the clinic. To view a particular record of diagnostic information (e.g., a record of defibrillation interventions), the physician uses the programmer interface to designate the record to be retrieved, and then initiate the retrieval. The programmer, in turn, interrogates the implantable device to cause the implantable device to transmit the selected record, and then receives and displays the selected record, typically in a graphical format, on the screen.

The physician, to optimize performance of the system, may need to view diagnostic data before reprogramming operating modes and parameter values. At times, a physician may have difficulty determining which diagnostic data will yield optimum information for a given patient. Uncertainty in selecting the correct data is often heightened by the limited amount of time physicians have to spend with individual patients. Sometimes it is impossible for a physician, faced with the wealth of diagnostic data, to evaluate with any degree of confidence how well or appropriately a cardiac stimulator has operated in the programmed operating modes and parameter values.

For example, assuming that no adjustments are made to the implantable device parameters, it will typically take the physician 20 to 25 minutes to sequence through the steps of the follow-up protocol. This is due in-part to the need for the physician to interactively specify each diagnostic record to be retrieved, and then wait for the programmer to retrieve and display the data record. In addition to affecting the physician's efficiency, this time penalty is often burdensome to the patient, since the patient typically must hold the telemetry wand in place throughout most or all of the procedure.

Another problem with the current practice is that the physician often fails to retrieve and evaluate clinically significant diagnostic data records stored within the implantable device. It is currently common practice for the physician to retrieve certain diagnostic data records only if the patient is or reports a symptomatic event. As a result, clinically significant data is frequently overlooked during the diagnostic decision process. One reason for this under-utilization of diagnostic information is the amount of time required, to retrieve and review each diagnostic record. Another reason is due to the storage of very large diagnostic data records in the implantable device memory. Because these records are not organized in a logical user-friendly manner, it is burdensome for the physician to view all of the available diagnostic records and determine their relevancy to the patient under consideration.

One approach to solving this problem is taught in U.S. Pat. No. 5,833,623, System and method for facilitating rapid retrieval and evaluation of diagnostic data stored by an implantable medical device, issued to Mann, et al. and hereby incorporated by reference in its entirety. That invention addresses the issues via software incorporated into an implantable device programmer that has a variety of inter-related features for automating and permitting the customization of the follow-up evaluation process. This solution provides the opportunity for the physician to create a customized protocol that eases the burden on the physician to retrieve relevant diagnostic data. A similar approach is described in aforementioned "Medtronic Kappa® Pacemaker Programming Guide" wherein is described a "Checklist" approach to customize a protocol to ease the follow-up burden. In both cases, the ultimate goal is to ensure the compliance of the physician, clinician, or technician to a standardized protocol. Neither approach eases the burden of organizing the immense diagnostic data into a more usable format. While currently available graphical format adopted by all manufacturers eases the interpretation process, all the recorded device data into a time-based approach that simplifies the selection of the appropriate record(s) for the busy physician is not available.

An alternative solution, known to those skilled in the art, involves the implantation or co-implantation of a medical device that records the patient's cardiac rhythm over a set of time periods, as described in U.S. Pat. 6,102,874, Implantable medical device for tracking patient functional status, issued to Stone, et al, and incorporated herein by reference in its totality. These devices, however, merely record the patient's cardiac rhythm when triggered either by the patient or by a set of events. There is a limit to the number of episodes that can be collected and captured for later interrogation and display on a programmer. Moreover, such episodes will not be captured or displayed under any particular category. Thus, for example, it is left in the hands of a busy physician to interpret the stored ECG/EGM and determine if and when defibrillation therapy was delivered.

The present invention provides, inter alia, various structures and methods to overcome the limitations of the prior art.

SUMMARY OF THE INVENTION

The present invention facilitates the task of accessing a patient's therapy history by organizing stored data into convenient categories related to the time the episodes and events were captured. These categories currently include, but are not limited to, the following organizational classifications: Checkup, Implant, Therapy, Medical, Magnet, and ICD Alert data/information. The categories are arranged in chronological order on a display screen of the programmer or an external device such that the oldest information (from Implant) appears under an icon on the extreme left side of the screen, with the most recent information on the right side of the screen. As the memory capacity of an implanted pacemaker or ICD devices increases, it is certain that these categories will be expanded. The present invention provides scalability for such expanded memory.

In one aspect of the present invention, upon selecting a "Time Line" display screen, the user initiates a programmer's selection apparatus to choose a desired icon which action, in turn, reveals a corresponding detailed information stored under that category. For example, the physician may select the "Therapy" icon to get an idea of the frequency and episodes of defibrillation therapies and how these relate to the ICD Alerts. Accordingly, the physician might wish to toggle between the "Therapy" and "ICD Alert" icons. The episodes, therapies, and alerts may be aligned to indicate the same time and date.

In yet another aspect of the invention, a physician may need to determine whether a change in medication has had a favorable impact on the number and/or frequency of the ventricular arrhythmia. The physician may only, for example, wish to determine whether the onset of an AV nodal tachycardia had preceded an ventricular arrhythmia. In this case, the physician would simply drill down into the data accumulated under the "Therapy" icon to access the relevant recorded data.

The foregoing features are some of the representative distinguishing elements of the present invention. These features will be more readily understood by referring to the following detailed description of preferred embodiments and figures.

DETAILED DESCRIPTION OF THE DRAWINGS

Figure 1:
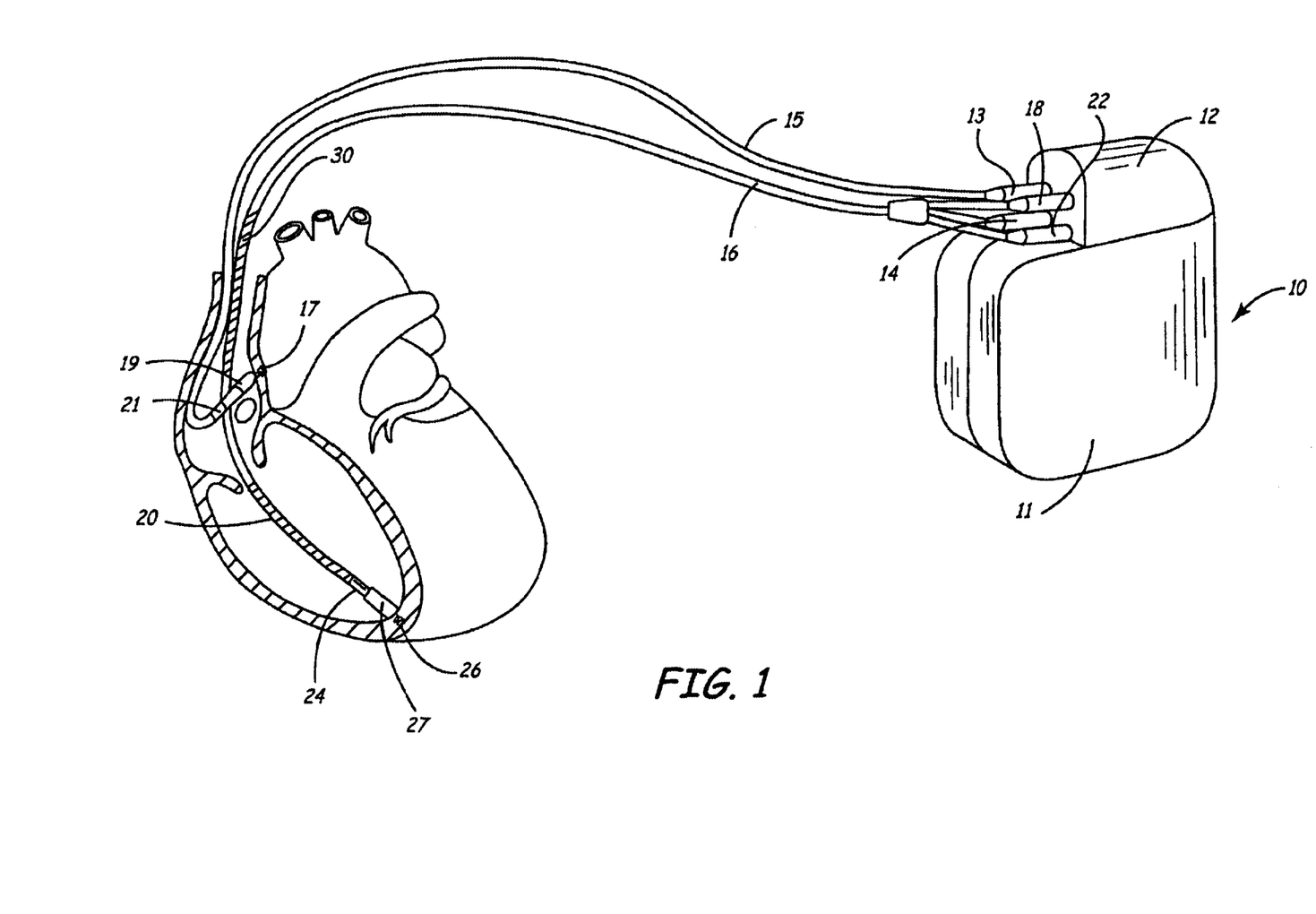
FIG. 1 is an illustration of a PCD type system according to the present invention.

Referring now to FIG. 1, there are illustrated a defibrillator 10 and leads 15 and 16, making up the PCD type system of this invention. The leads shown are illustrative, it being noted that other specific forms of leads are within the scope of this invention. See, for example, U.S. Pat. Nos. 4,932,407 and 5,174,288, as well as 5,261,400, all of which are incorporated by reference. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for sensing ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation.

Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SCV coil 30, positioned in the subclavian vein, which can be used for R wave sensing and/or applying cardioversion pulses. Lead 16 carries respective concentric coil conductors (not shown), separated from one another by appropriate means such as tubular insulative sheaths and running the length of the lead for making electrical connection between the PCD device 10 and respective ones of electrodes 20, 24, 26 and 30.

Atrial lead 15 as illustrated includes an extendable helix electrode 17 and a ring electrode, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An implantable PCD type device, or defibrillator 10, is shown in combination with atrial and ventricular leads, with the lead connector assembly 13,14, 18, and 22 being inserted into the connector block 12 of the device 10. A specific example of a defibrillation pulse generator that may be used in conjunction with the present ventricular lead is disclosed in U.S. Pat. No. 4,953,551. Other PCD type units can be used; reference is made to U.S. Pat. Nos. 5,163,427 and 5,188,105 as disclosing illustrative forms of apparatus for delivering cardioversion and defibrillation pulses. As used herein, the term "PCD type" device refers to any device that can apply both pacing therapy and shock therapy for controlling arrhythmias.

Figure 2:
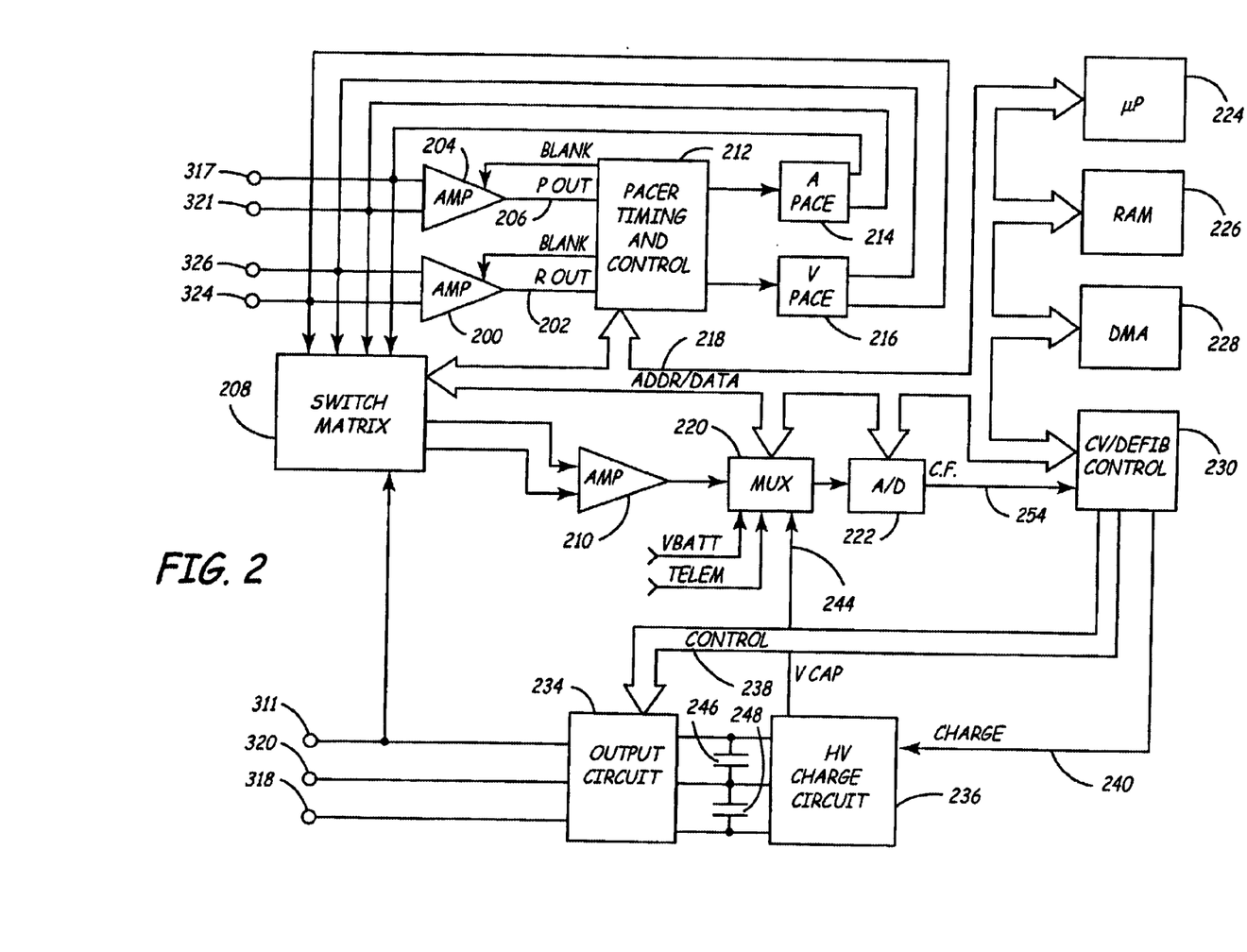
FIG. 2 is a block, functional diagram of a PCD type device adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the PCD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the implantable PCD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
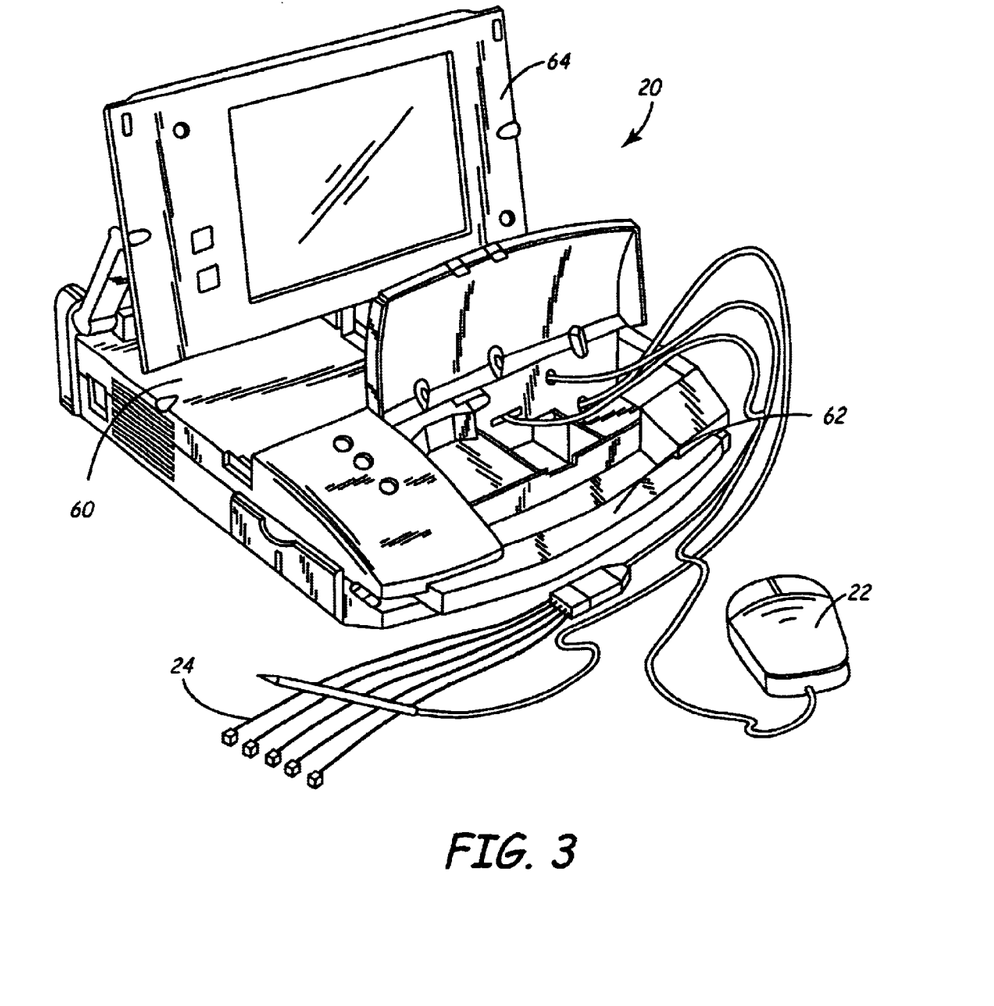
FIG. 3 is a perspective view of the external programming unit of FIG. 1.

FIG. 3 is a perspective view of programming unit program 20 in accordance with the present invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 3, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 3 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming unit with which the present invention may be advantageously practiced.

Figure 4A:
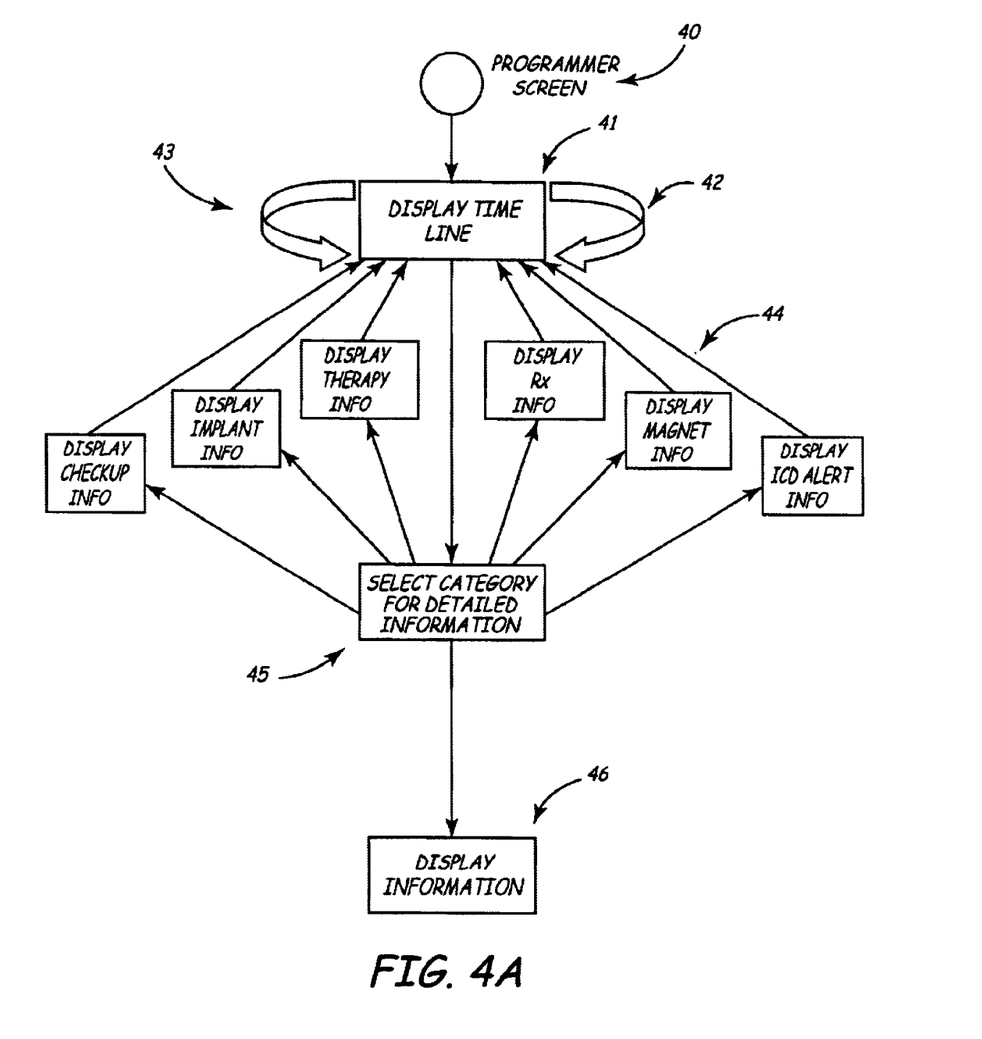
FIG. 4A and FIG. 4B show a control flow chart of the present invention.

FIG. 4A is a flow chart representing a high-level control logic/scheme of the present invention. The user (physician, clinician, or technician) initiates control screen 40 to select initial Time Line screen 41 from a menu. Thereafter, the user is able to access interactive features 42 and 43 for a forward or backward scroll, respectively. As will be discussed in FIGS. 5 and 6, the user is able to scroll forward and backward in time to select those events of interest within a particular time frame. Upon returning to Time Line screen 41, the user then may use the forward/backward update capability to more easily find the time span of interest.

After activating a particular time frame, the user may then select the category of interest 44 to access and display information available under control logic 46. After accessing data in the selected category the user can print the data using a print menu (not shown). This information may be used for purposes of diagnostic or evaluation of device performance. Further, the user may close category 44 to return to Time Line screen 41 for selection of another category, as needed.

Figure 4B:
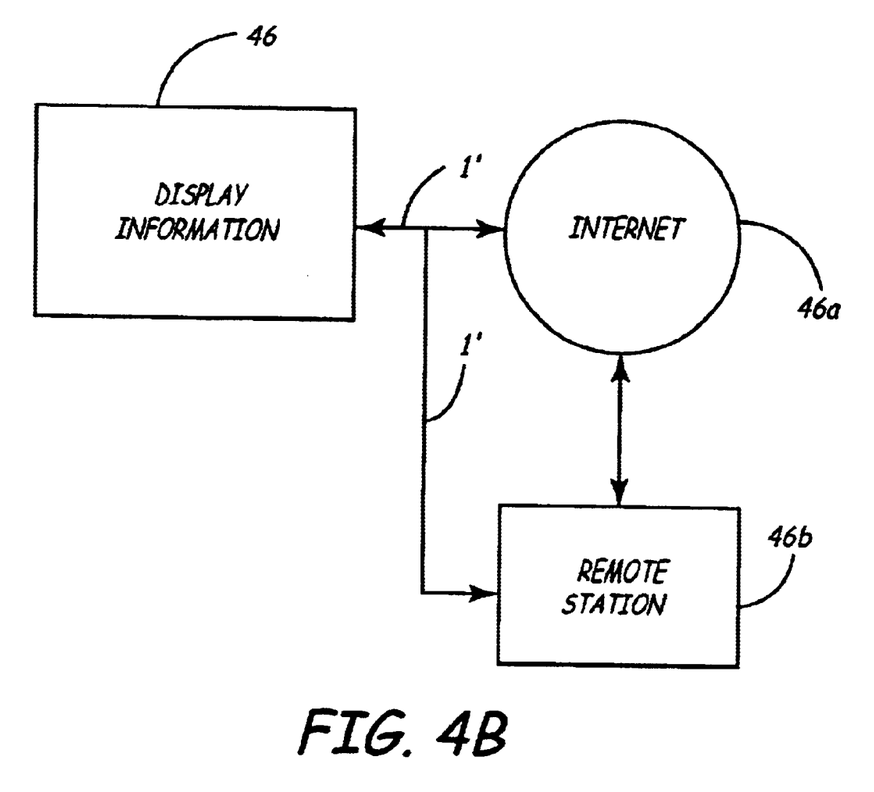

FIG. 4B is an embodiment in which display information 46 may be routed via a communication platform such as the Internet 46a generally representing the Internet, intranet, extra net and the World Wide Web or equivalent. Remote station 46b may be directly interactive with internet 46a or, in the alternate, may have direct data communication with display information 46 via communication interface I'.

Remote station 46b is preferably manned by experts such as physicians and health care providers who manage the patient on a chronic basis, remotely. Interface I' may be any one of the communication systems including but not limited to modem, telemetry, cable, fiber optics, satellite, laser or equivalent.

Figure 5:
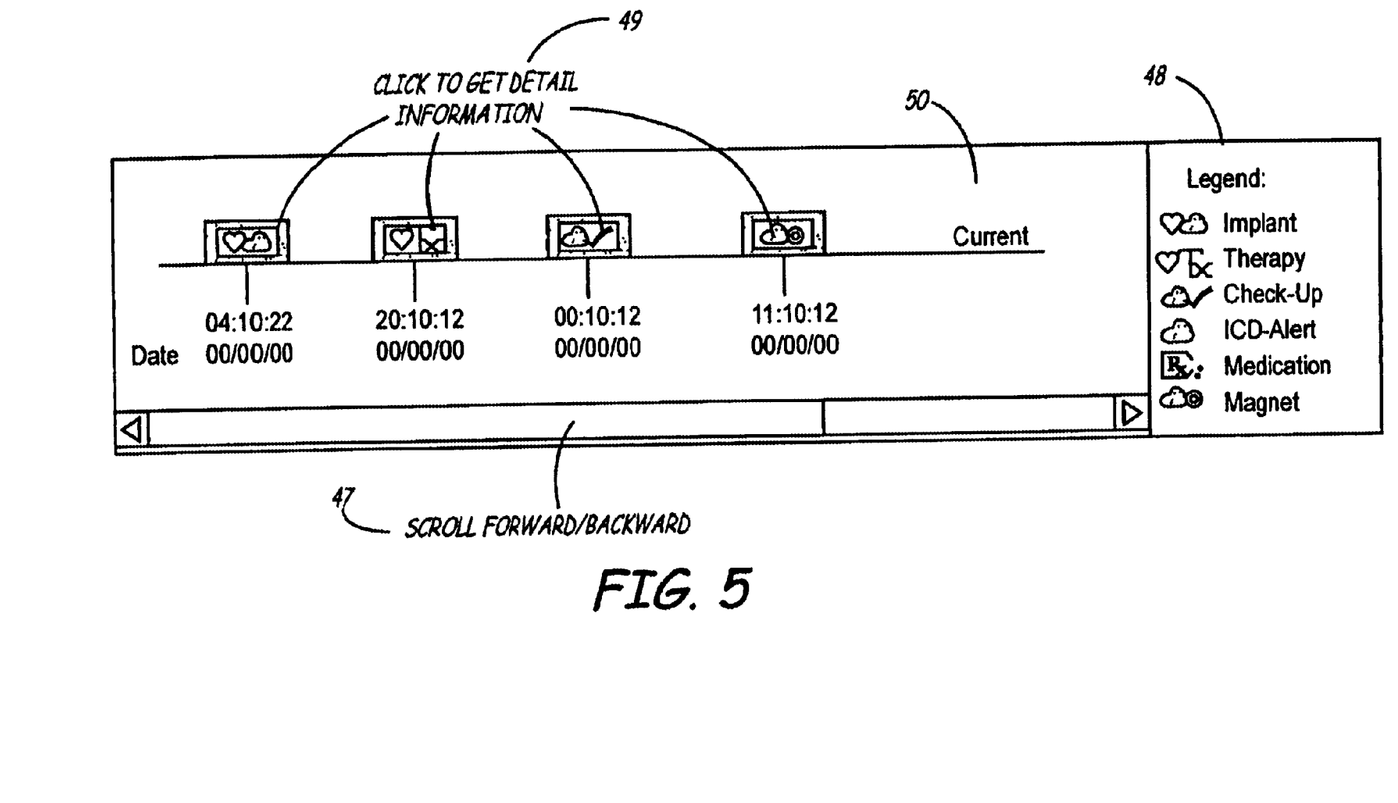
FIG. 5 is an illustration of the preferred embodiment of the initial Time Line screen.

FIG. 5 is an illustration of the preferred embodiment of the initial Time Line screen 41. Scroll bar 47 is similar to conventional graphical displays used on computer screens. Legend 48 depicts the possible icons which the user may select for display in the main portion of the screen. In accordance with the present invention, without limitation, the displayable icons include, for example, Implant, Therapy, Checkup, and Magnet icons. "Current" 50 is the portion of the screen on which the current date and time will be displayed. Such data is stored in the memory of the programmer and is always available for display on various screens of programmer 20.

As presently depicted, there are six data icons. As the need for further data and capabilities of the implanted ICDs expand, however, more icons will be added to meet additional needs and capabilities. Data available under the Implant icon 48 might include, for example, initial EGMs in which fibrillation is induced with the delivery of a defibrillation pulse as a record of what occurred with a successful recovery of normal sinus rhythm. Checkup icon 48 might include a record of changes to the programmed parameters as these occurred over the course of time. In other words, the data under this icon and that available under the Medication icon 48 would correspond with the patient's medical record. There are significant patient management advantages in having this data available in the device's memory. For example, if the patient is traveling and requires treatment, the physician need not call the patient's cardiologist or electrophysiologist for the patient's records, since these are available immediately upon interrogation of the device's memory under these icons. The data under Magnet icon 48 might include a record of the EGMs and/or ECGs that were taken over the course of time. These tracings are used to determine if the device's operational characteristics are within normal function. When the user selects one of these icons, including ICD Alert icon 48, a popup screen will immediately appear containing detailed information about the selected event or function.

Therapy data icon 48 contains larger data than those under the other icons. When the user selects this icon, a new screen (not shown) dedicated to Therapy history will appear. From this screen, the user may then highlight and select events of interest. For example, the user may wish to correlate a selection to what has been learned from examining the information under the ICD Alert icon 48. Various queries may be made to explore the historical data to determine the proper functioning of the ICD. For example, queries such as, without limitation, Did the alert result in undelivered therapy? Was that therapy successful? Was it a single therapy? Or was it an example of a situation that required multiple deliveries of defibrillation pulses? May be made to get answers from the stored data.

Figure 6:
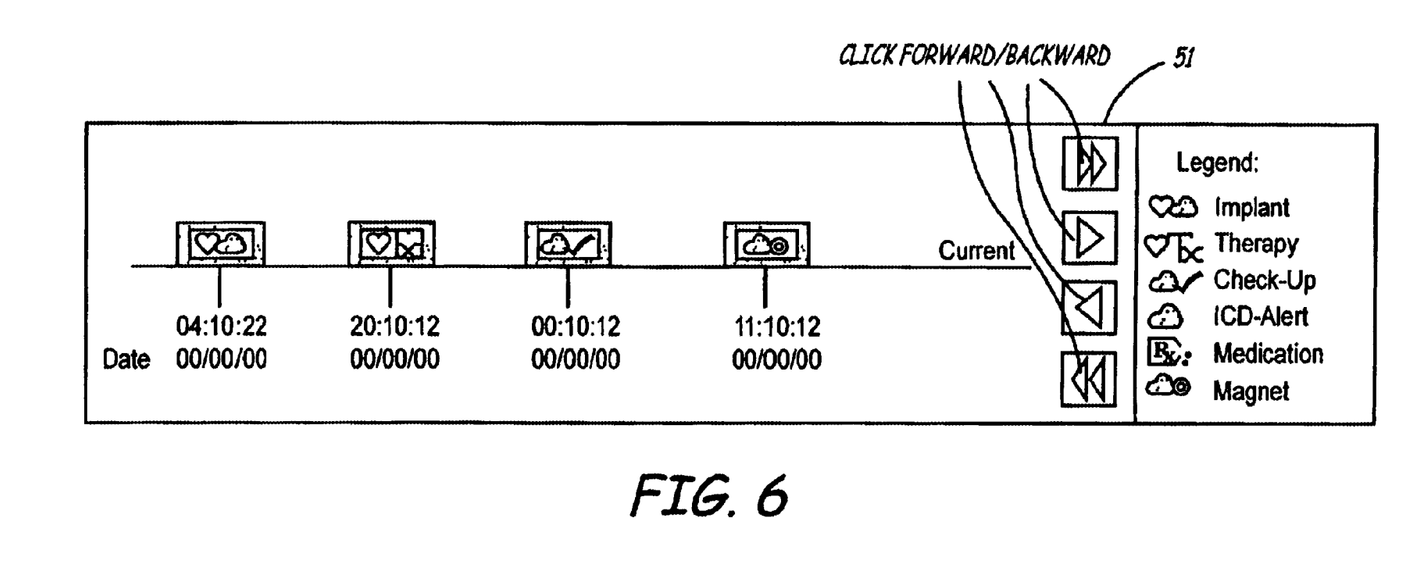
FIG. 6 is an illustration of an alternative embodiment of the initial Time Line screen.

Referring to FIG. 6, an alternate method of moving backward and forward through the timeline to access various events is shown. Icons 51 represent the following options: Move immediately to the most recent event; move one event forward; move one event backwards, and move immediately to the earliest event in the record. The use of these icons, as well as the scroll bar 47 illustrated in FIG. 5, provide timely access to the events of interest, thereby reducing the time of follow-ups. This in turn may result in substantial savings and operational efficiencies to various insurance companies and health care providers. In addition, the use of the Time Line approach itself will provide the physician fast and accurate access to items of interest, which should lead to more accurate medical diagnoses.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A method for medical record management comprising:
    accessing a medical record stored in an implantable medical device (IMD);
    categorizing the stored medical record in relation to at least one time line comprising a plurality of time frames, wherein said categorizing includes arranging the medical record under a time-ordered set of icons; and
    presenting the time line categorized medical record through an interactive navigation user interface providing for user activation of a particular time frame and selection of a category of interest to access and display information.

2. The method of claim 1 wherein said arranging includes selling the medical record under said icons in a chronological order.

3. The method of claim 1 wherein the interactive navigation user interface displays at least one graphical representation of events recorded and stored in the IMD.

4. The method of claim 3 wherein said display of said at least one graphical representation includes providing fast access to users to said events recorded and stored in the IMD.

5. The method of claim 1 wherein accessing a medical record stored in an implantable medical device comprises interrogation of the implantable medical device using an external device selected from a group consisting of a personal computer, a home monitor, and a programmer.

6. A software system implemented in at least one IMD to store therapy, diagnosis and physiological data and hosting a data communication with an external device having an application software to display at least one category relating to episode and event occurrence, the IMD-implemented software system comprising:
    means for interfacing with an external display device;
    means for time-line display of the data of the at least one category;
    means for selecting specific information within the at least one category; and
    means for interacting with said time-line display to navigate contents of the at least one category;
    said external device including said means for interfacing, said means for time-line display, said means for selecting and said means for interacting being in data communications to thereby communicate with the IMD and display data.

7. The system of claim 6, wherein said means for interfacing includes one of a programmer, a home monitor and a PC.

8. The system of claim 6 wherein said means for time-line display includes an interactive screen.

9. The system of claim 8 wherein said interactive screen includes visual display icons related to the at least one category.

10. The system of claim 9 wherein said visual display icons include a time line display for device information, therapy information, check-up routine information, IMD alert events, medication information and IMD telemetry information.

11. The system of claim 6 wherein said means for selecting includes a plurality of interactive screens and means.

12. A medical data communication system to remotely access data stared in at least one implantable medical device and provide a time-line display of therapy, diagnosis and physiological data, comprising:
    means for interfacing an implantable medical device with an external display device;

means for transmitting data from the external display device to a remote location; and means for viewing the transmitted data on a time-line display; wherein said means for viewing includes an interactive screen wherein said time-line display is navigable to review the data for device information, therapy information, check-up routine information, implantable medical device alert events, medication information and implantable medical device telemetry information.

13. The communication system of claim 12 wherein said interfacing means includes one of a programmer, a home monitor and an instrument in wireless data communications with the implantable medical device.

14. The system of claim 12 wherein said time-line display includes visual screen icons.

15. The system of claim 12 wherein said means for transmitting includes a data communication connection selected from a group consisting of an Internet connection, an intranet connection, and an extranet connection.

16. The system of claim 15 wherein said transmitting means includes a link selected from a group consisting of a modem, a cable, a wireless telemetry, a satellite, a fiber optics, and a laser systems.

* * * * *